US005824015A

United States Patent [19]
Sawyer

[11] Patent Number: 5,824,015
[45] Date of Patent: *Oct. 20, 1998

[54] METHOD FOR WELDING BIOLOGICAL TISSUE

[75] Inventor: Philip N. Sawyer, Brooklyn, N.Y.

[73] Assignee: Fusion Medical Technologies, Inc., Mountain View, Calif.

[*] Notice: The term of this patent shall not extend beyond the expiration date of Pat. No. 5,156,613.

[21] Appl. No.: 461,227

[22] Filed: Jun. 5, 1995

Related U.S. Application Data

[63] Continuation of Ser. No. 231,998, Apr. 21, 1994, abandoned, which is a continuation of Ser. No. 832,171, Feb. 6, 1992, abandoned, which is a continuation-in-part of Ser. No. 654,860, Feb. 12, 1991, Pat. No. 5,156,613.

[51] Int. Cl.$^6$ .................................................... A61B 17/00
[52] U.S. Cl. ............................. 606/214; 606/213; 606/8; 606/40; 606/154
[58] Field of Search ............................... 424/400; 606/7, 606/8, 10, 12, 17, 213, 214, 40, 3, 215, 153, 154, 155, 32; 128/898

[56] References Cited

U.S. PATENT DOCUMENTS

| 2,011,169 | 8/1935 | Wappler | 174/89 |
|---|---|---|---|
| 2,510,205 | 6/1950 | Baird | 219/8 |
| 2,618,267 | 11/1952 | Hanriot | 128/303 |

(List continued on next page.)

FOREIGN PATENT DOCUMENTS

| 330 135 | 8/1989 | European Pat. Off. . |
|---|---|---|
| 405 429 | 2/1991 | European Pat. Off. . |
| 480 293 | 4/1992 | European Pat. Off. . |
| 526 756 | 2/1993 | European Pat. Off. . |
| 640 315 | 3/1995 | European Pat. Off. . |
| 4-288165 | 10/1992 | Japan . |
| 1091933 | 5/1984 | U.S.S.R. . |
| WO 91/04073 | 4/1991 | WIPO . |
| WO 92/02238 | 2/1992 | WIPO . |
| 93/03793 | 3/1993 | WIPO . |
| 93/17669 | 9/1993 | WIPO . |

OTHER PUBLICATIONS

Chemical Abstacts, vol. 114, No. 5, 38493y, (1990).
S. Shapiro et al., "Microvascular End–to–side Arterial Anastomosis Using the Nd:YAG Laser," Neurosurgery, vol. 25, No. 4 (1989) pp. 584–589.
T. Benke et al. "Comparative Study of Suture and Laser–Assisted Anastomoses in Rat Sciatic Nerves," Lasers in Surgery and Medicine, 9:602–615 (1989).
Popp et al. "Welding of Gallbladder Tissue With a Pulsed 2.15 μm Thulium–Holmium –Chromium: YAG Laser," Lasers in Surgery and Medicine, 9:155–159 (1989).
Oz et al. "Tissue Soldering by Use of Indocyanine Green Dye–enhanced Fibrinogin With the Near Infrared Diode Laser" Journal of Vascular Surgery vol 11, No.5, pp. 718–725 (1990).
Libutti et al., "Canine Colonic Anastomoses Reinforced With Dye–enhanced Fibrinogen and a Diode Laser," Surgical Endoscopy, vol. 4, No. 2, pp. 97–99 (1990).
Oz et al., "Effects of a 2.15 –Micron Laser on Human Atheroscherotic Xenografts in Vivo," Angiology, The Journal of Vascular Diseases, vol. 41, pp. 772–776 (1990).

(List continued on next page.)

Primary Examiner—Raj Bawa
Attorney, Agent, or Firm—Townsend and Townsend and Crew LLP

[57] ABSTRACT

A method for joining or reconstructing biological tissue comprises providing a solid filler material in the form of a preformed sheet, where the sheet comprises collagen, gelatin or a mixture thereof. The filler material is placed over tissue. Radiofrequency energy or optical energy is thereafter applied to the filler material in an amount sufficient to melt or denature the filler material.

12 Claims, 9 Drawing Sheets

U.S. PATENT DOCUMENTS

| | | | |
|---|---|---|---|
| 2,708,933 | 5/1955 | August | 128/303 |
| 2,808,833 | 10/1957 | August | 128/303 |
| 3,527,224 | 9/1970 | Rabinowitz | 128/334 |
| 3,578,939 | 5/1971 | Green | 219/74 |
| 3,742,955 | 7/1973 | Battista | 128/334 |
| 3,834,392 | 9/1974 | Lampman et al. | 128/303 |
| 3,858,586 | 1/1975 | Lessen | 128/303 |
| 3,903,891 | 9/1975 | Brayshaw | 128/303 |
| 3,991,764 | 11/1976 | Incropera et al. | 128/303 |
| 4,040,426 | 8/1977 | Morrison, Jr. | 128/303 |
| 4,060,088 | 11/1977 | Morrison et al. | 128/303 |
| 4,100,390 | 7/1978 | Jackson | 219/74 |
| 4,618,885 | 10/1986 | Nagasaki et al. | 358/98 |
| 4,633,870 | 1/1987 | Sauer | 128/303.1 |
| 4,638,800 | 1/1987 | Michel | 128/303 |
| 4,640,279 | 2/1987 | Beard | 128/303 |
| 4,672,969 | 6/1987 | Dew | 606/8 |
| 4,708,137 | 11/1987 | Tsukagoshi | 128/303 |
| 4,733,660 | 3/1988 | Itzkan | 606/17 |
| 4,781,175 | 11/1988 | McGreery et al. | 128/303 |
| 4,854,320 | 8/1989 | Dew | 606/213 |
| 4,878,492 | 11/1989 | Sinofsky | 606/7 |
| 4,889,120 | 12/1989 | Gordon | 306/216 |
| 4,892,098 | 1/1990 | Sauer | 606/8 |
| 4,901,720 | 2/1990 | Bertrand | 606/40 |
| 4,929,246 | 5/1990 | Sinofsky | 128/303 |
| 4,930,504 | 6/1990 | Diamantopoulas et al. | 606/3 |
| 4,943,290 | 7/1990 | Rexroth et al. | 606/45 |
| 5,002,051 | 3/1991 | Dew | 606/12 |
| 5,021,452 | 6/1991 | Labbe et al. | 514/474 |
| 5,041,110 | 8/1991 | Fleenor | 606/34 |
| 5,071,417 | 12/1991 | Sinofsky | 606/10 |
| 5,140,984 | 8/1992 | Dew et al. | 128/395 |
| 5,201,745 | 4/1993 | Tayot et al. | 606/151 |
| 5,207,670 | 5/1993 | Sinofsky | 606/8 |
| 5,207,691 | 5/1993 | Nardella | 606/142 |
| 5,209,776 | 5/1993 | Bass et al. | 106/124 |
| 5,219,895 | 6/1993 | Kelman et al. | 522/68 |
| 5,272,716 | 12/1993 | Soltz et al. | 372/109 |
| 5,290,272 | 3/1994 | Burstein et al. | 606/4 |
| 5,292,253 | 3/1994 | Levy | 433/215 |
| 5,292,362 | 3/1994 | Bass et al. | 106/124 |
| 5,330,974 | 7/1994 | Pines et al. | 514/21 |
| 5,334,191 | 8/1994 | Poppas et al. | 606/12 |
| 5,336,221 | 8/1994 | Anderson | 606/27 |
| 5,354,323 | 10/1994 | Whitebook | 607/89 |
| 5,354,336 | 10/1994 | Kelman et al. | 623/6 |
| 5,372,585 | 12/1994 | Tiefenbrun et al. | 604/59 |
| 5,403,312 | 4/1995 | Yates et al. | 606/50 |
| 5,409,481 | 4/1995 | Poppas et al. | 606/12 |
| 5,410,016 | 4/1995 | Hubbell et al. | 528/354 |
| 5,421,923 | 6/1995 | Clarke et al. | 156/73.1 |

OTHER PUBLICATIONS

Bass et al., "Anastomosis of Biliary Tissue with High–Frequency Electrical Diathermy," Surgical Endoscopy, vol. 4, No. 2, pp. 94–96 (1990).

Oz et al, "A Fiberoptic Compatable Midinfrared Laser with $CO_2$ Laser–like Effect: Application to Atherosclerosis", Journal of Surgical Research, vol. 17, No. 6, pp. 493–501 (1989).

Oz et al. "Strength of Laser Vascular Fusion: Preliminary Observations on the role of Thrombus," Lasers in Surgery and Medicine vol 10, pp. 393–395 (1990).

Chuck et al, "Dye–Enhanced Laser Tissue Welding", Lasers in Surgery and Medicine, vol. 9, pp. 471–477 (1989).

Oz et al., "In Vitro Comparison of Thulium–Holmium–Chromium: YAG AND Argon Ion Lasers for Welding of Biliary Tissue," Lasers in Surgery and Medicine, vol. 9, pp. 248–253 (1989).

Treat et al., "Preliminary Evaluation of a Pulsed 2.15 $\mu$m Laser System for fiberoptic Endoscopic Surgery," Lasers in Surgery and Medicine, vol. 8, pp. 322–326 (1988).

Bass et al., "Sutureless Microvascular Anastomosis Using the THC: YAG Laser: A Preliminay report," Microsurgery vol. 10, pp. 189–193 (1989).

Becker et al., Radiofrequency Balloon Angioplasty Rationale And Proof Of Principle, Invest. Rad. vol. 23, No. 11, pp. 810–817 1988.

Barry et al., The Effect Of Radiofrequency –Generated Thermal Energy On The Mechanical And Histologic Characteristics Of The Arterial Wall In Vivo, Rad. Ang. vol. 117, No 2, pp. 332–341, Feb., 1989.

Lee et al., Thermal Compression And Molding Of Atherosclerotic Vascular Tissue With Use Of Radiofrequency Energy, JACC vol. 13, No. 5, pp. 1167–1175, Apr. 1989.

Dennis et al., (1979) Evaluation of Elecrofulguration in Control of Bleeding of Experimental Gastric Ulsers, Digestive Diseases and Sciences 24:11:845–848.

Hendry et al., (1993) Argon Beam Coagulation Compared with Cryoablation of Ventricular Subendocardium, Ann. Thorac. Surg. 55:135–139.

Oz et al., (1990) Progress in Biomedical Optics SPIE 1200:55–59.

Costello et al., "Sutureless End–to–End bowel Anastomosis Using Nd:YAG and Water–Soluble Intraluminal Stent," (1990), Laser in Surgery and Medicine, vol, 10, pp. 179–184.

Poppas et al., "Laser Welding in Urethral Surgery: Improved Results with a Protein Solder," (1988), J. Urology, vol. 139(2), pp. 415–417.

Khadem et al., "Photoynaic Biologic Tissue Glue", 1994, Cornea, vol. 13, No. 5, pp. 406–410.

Sensaki et al., "Laser Patch Welding: Experimental Study for Application to Endoscopic Closure of Bronchopleural Fistula, a Preliminary Report", 1995, Laser in Surgery and Medicine, vol. 16, pp. 24–33.

Kirsch et al., "Preliminary Results of Laser Tissue Welding in Extravesical Reimplantation of the Ureters", 1994, The Journal of Urology, vol. 151, pp. 514–517.

Poppas et al., "Preparation of Human Albumin Solder for Laser Tissue Welding", 1993, Lasers in Surgery and Medicine, vol. 13, pp. 577–580.

Poppas et al., "Patch Graft Urethroplasty Using Dye Enhanced Laser Tissue Welding With A Human Protein Solder: A Preclinical Canine Model", 1993, The Journal of Urology, vol. 150, pp. 648–650.

Wilder et al., "Skin Closure with Dye–Enhanced Laser Welding and Fibrinogen", 1991, Plastic and Reconstructive Surgery, vol. 88, No. 6, pp. 1018–1025.

METHOD FOR WELDING BIOLOGICAL TISSUE

CROSS REFERENCE TO RELATED APPLICATIONS

The present application is a continuation of application Ser. No. 08/231,998, filed on Apr. 21, 1994, now abandoned, which was a continuation of application Ser. No. 07/832,171, filed on Feb. 6, 1992, now abandoned, which was a continuation-in-part of application Ser. No. 07/654,860, filed on Feb. 12, 1991, now U.S. Pat. No. 5,156,613.

BACKGROUND OF THE INVENTION

1. Technical Field

The present invention relates to the use of laser emitted optical energy or radio frequency ("RF") energy for joining, repairing or reconstructing biological tissue. In particular, the present invention relates to a method of utilizing a welding rod filler material in combination with such optical or RF energy to join, repair or rebuild biological tissue.

2. Background Art

Optical energy, in particular that generated by lasers, has been applied and utilized in the medical field for a variety of surgical purposes. The medical industry initially utilized industrial lasers for the destruction of tumors or surface lesions in patients. At that time, the lasers were relatively crude, high powered and ineffective for delicate internal biological applications.

Subsequently, a variety of cauterization techniques were developed utilizing either laser or RF techniques. Laser optical energy was also utilized to reduce the flow of blood in an open wound or in a surgically created incision: the optical energy being supplied in sufficient quantity to sear or burn the blood vessels thus sealing the open ends of the capillaries and preventing blood flow. A typical use of laser cauterization is described in U.S. Pat. No. 4,122,853. Again, the types of lasers utilized at that time provided very high power application and very high wattage with the surrounding tissue also being destroyed, thus causing longer healing times, infection and scarring.

As newer, lower powered lasers were developed, techniques were developed for atheroma ablation or other endarterectomy procedures for blood vessels. One such procedure is disclosed in U.S. Pat. No. 4,878,492. The $CO_2$, YAG and Excimer lasers all provided substantial improvements in these procedures due to their lower power output. These more sophisticated devices each provide better aiming of a narrower optical energy beam such that destruction of the walls of the blood vessels can be minimized. Also, advances in optical fiber technology allowed the surgeon to direct more accurately the optical energy to the desired location with greater precision.

Lasers have also been used to "glaze" the internal surfaces of blood vessels after balloon dilation and laser angioplasty in an attempt to prevent medical recollapse, intimal fibroplasia, and reobliteration.

Another procedure which has been developed includes the use of optical energy for welding or otherwise joining or connecting biological tissue. The original attempts to carry out these procedures began in the late 1960's and almost all universally met with failure not so much because of an inability to weld or join the tissue together, but because of the weakness of the resulting weld. The use of the lower powered laser devices, either alone or in combination with physiologic solutions, however, allowed the surgeon to cool the weld site sufficiently to obtain slight improvements in weld strength. Furthermore, RF energy has recently been utilized in both uni- and bi-polar generators to attempt to "weld" or "solder" biological tissue.

U.S. Pat. No. 4,672,969 discloses one method and apparatus for utilizing laser emitted optical energy to effect wound closure or other reconstruction of biological tissue by applying the optical energy to produce thermal heating of the biological tissue to degree suitable for denaturing the tissue proteins such that the collagenous elements of the tissue form a "biological glue" which seals the tissue to effect the joining. This glue is later reabsorbed by the body during the healing process. The patent discloses a number of different types of lasers with preference stated for the Nd:YAG type, because its particular wavelength allows optical energy to propagate without substantial attenuation through water and/or blood for absorption in the tissue to be repaired.

Despite these improvements, however, the weakness of the weld joint still remains as the primary disadvantage of this procedure and extensive current research is being conducted in an attempt to improve on that deficiency. I have now invented a simple yet elegant welding procedure for biological tissue utilizing laser or RF energy which overcomes the shortcomings of the prior art.

SUMMARY OF THE INVENTION

The present invention relates to a method of joining or reconstructing biological tissue which comprises applying energy to the biological tissue while providing a suitable filler material thereto; denaturing or melting the filler material and adjacent biological tissue with the energy to cause mixing of the denatured or melted filler material and biological tissue, thus joining or reconstructing such tissue.

The filler material is preferably collagen and one embodiment of the inventive method includes adhesively attaching the collagen filler material to the biological tissue to assure proper placement thereupon. This may be achieved by applying the collagen material adjacent the biological material with fibrin glue or other biological tissue adhesive.

This method may also include applying an energy absorption aid to one of the filler materials or the biological tissue, or both, to facilitate absorption of the applied energy thereby. Generally, the energy absorbing aid is applied to preselected locations prior to the application of energy thereto, and it also assists in visually determining the areas to be joined or reconstructed. Preferred energy absorbing aids include dyes, such as Vital Green or Basic Red, blood or water.

Often, the biological tissue includes an incision and the method enables the surgeon to enclose the incision by the mixing and joining of the denatured or melted filler material and biological tissue. If desired, spaced sutures may be placed in tissue surrounding the incision to fix the position of adjacent tissue.

The filler material may be prepared by dissolving a predetermined amount of collagen material in water to form a solution, followed by drying or freeze drying of the solution in the desired form and shape of the collagen filler material. Preferably, the collagen material used to prepare the filler material is a mixture of an insoluble collagen material and a soluble collagen material in a weight ratio of about 1:3 to 3:1.

The present method also contemplates applying a physiologically acceptable solution to one of the collagen filler materials or the biological tissue to control the temperature of the joint due to the energy imparted thereto. The applied energy may be provided as optical energy (i.e., by a laser), from an RF generator, or by an inert gas beam coagulator, since these devices have sufficient power dissipation to cause the energy or heat that they produce to be absorbed by the tissue and collagen filler material. The heat provided by the coagulator (or which is converted from the applied laser or RF energy) generally should be within a range bounded by the minimum absorption rate at which the protein elements of the tissue and collagen filler material are converted to melted collagen and by a maximum absorption rate which would cause water in the tissue or collagen filler material to boil. The RF energy may be provided by uni- or bipolar techniques, since each will melt the collagen filler material into the defect or joint area. Thus, the protein elements of the tissue and the collagen filler metal can be melted or denatured, mixed or combined, and then cooled to form a weld joint.

When the biological tissue includes a lesion, the method further comprises forming a seal of collagen material near or upon the lesion. When the lesion comprises at least two separated segments of biological tissue, the method further comprises placing the two segments of tissue in close proximity, and guiding the energy source and collagen filler material into the area of their junction for joining or reconstruction thereof.

BRIEF DESCRIPTION OF THE DRAWINGS

The features and advantages of the present invention are more readily understood when read in conjunction with the attached drawing figures wherein.

DETAILED DESCRIPTION OF THE PREFERRED EMBODIMENTS

It is well known that biological tissue includes cell layers in a protein framework which provides tensile strength. The proteins are amino acids, and it is known that the application of heat or optical energy can denature such proteins. When the source of heat or energy is removed, the proteins if not totally broken down cool and begin to reconfigure and form an approximate replication of the prior tissue structure.

The prior art teaches that the application of either optical energy from a laser or RF energy from a suitable generator could be used to bring the temperature of the biological tissue above room temperature but below the boiling point of water (preferably between 45°–75° C. and more prefer 60°–70° C.). The denaturing of collagen, a major source of protein in the human body, can also be achieved by the application of energy, and is believed to go into solution and form a type of "biological glue" which seals the incision or discontinuity in the biological tissue. Thus, it is possible to seal lesions, anastomose a severed or incised vessel or to reconstruct diseased or damaged tissue.

I have found that a major disadvantage of such laser welding procedures for rejoining incised tissue is that insufficient tissue material is present for completing a successful joint. When optical energy from the laser actually denatures or melts the tissue in the areas to be joined, a portion of the tissue thickness is reduced so that the denatured materials can flow towards each other and stick together to form the joint. On relatively thin sections of tissue to be joined, such as in repairing an incised blood vessel wall, there is insufficient denatured material in the joint area for providing a sound, high tensile strength connection.

Collagen is known for use in the medical field as a material for repairing tissue damage caused by thermal, chemical or mechanical trauma (see, e.g., "Collagen: Its Place In the Medical Industry" by J. M. Pachence, et al., Medical Device and Diagnostic Industry, January, 1987). I have found that this material can be used as a filler which can be placed in the path of the laser beam, melted or denatured, and directed into the incision or the tissue which is to be reconstructed. Bipolar or unipolar RF energy will also yield the same or substantially similar results. Based on qualitative observations, the additional collagen molecules provided by the filler material allows the tensile strength of the welded incision to be significantly increased.

The application of optical energy and the use of additional collagen material provides several advantages in addition to increased tensile strength. The healing time of the wound is accelerated because blood supply to the affected tissue can be reestablished immediately after the surgical procedure. In addition, little or no scarring is produced because sutures are eliminated or substantially minimized. Furthermore, the various techniques disclosed herein enhance the accuracy of the welding procedure thus avoiding optical or RF energy damage to adjacent or unintended areas of such tissue.

A wide variety of materials may be used as a filler in this welding procedure. The most common source is collagen which may be obtained from bovine hides. Another material, which is ideal from the standpoint of melting, flowing, and compatibility with biological tissue, is a collagen-like substance which has been modified by dissolving collagen in water and modifying the thusly dissolved collagen to render its surface charge effectively more positive than prior to modification. This material is well known and is disclosed, e.g., in U.S. Pat. No. 4,238,480. The modified collagen is freeze-dried to form a solid mass of gelatin. In accordance with the teachings of the present invention, this mass of gelatin, alone or in combination with other collagen material, may be formed in the shape of a rod, strip, film or flake and utilized as a filler in a laser welding procedure.

Other forms of collagen which are suitable for use in the present invention include Semed F, a collagen preparation manufactured in native fiber form without any chemical or enzymatic modifications, and Semed S, a lyophilized collagen powder extracted from fresh bovine hides. Each of these products is available from Semex Medical, Frazer, Pa. The Semed F material is a Type I collagen (greater than 95%), while the Semed S is a mixture of Type I and Type III collagen macromolecules in which the shape and dimension of tropocollagen in its natural helical orientation is retained.

Either of the Semed S and Semed F collagen material may be formed into welding filler material by suspending a suitable amount (usually between about 0.5 and 10 weight percent) of the material in deionized water to form a viscous solution followed by drying the solution under the action of heat or by freeze-drying of the solution, followed by vacuum treating and heating steps. As above with the gelatin material, the final shape of the material can be in the form of a rod, strip, powder, etc. A paste formulation may also be formed by dissolving relatively large amounts of the material in relatively small amounts of saline or deionized water.

The shapes of these formed materials are solid and soft but firm. These materials may be readily sliced or cut to the desired sizes for use in the laser welding procedure. Also, the desired size and shape can be achieved by freeze-drying the material in a suitably sized mold which is configured to the desired size and shape of the product. The thicknesses of the rods or sheets can be between ¼ and 2 mm, depending upon the size of the incision to be joined or area of tissue to be reconstructed. When the paste form is utilized, it may be painted or dropped onto the areas of tissue to be joined or reconstructed. Thus, the surgeon can choose from a wide variety of shapes, sizes, densities, thicknesses and configurations of such filler material depending upon the type of tissue to be welded.

The concentration of the collagen in the liquid which is to be freeze-dried can range from 0.5–10% and preferably 1–5%, with the lower concentrations forming less dense or discontinuous solids. At lower concentrations of 0.5 to 1%, the Semed F forms a structure which approximates dense cobwebs.

Native collagen film, wherein the film strength is preserved and the triple-helix structure of the collagen polymer is maintained intact, can also be used, either alone or with a plasticizer incorporated therewith. A typical collagen sheet is cast from solution to a thickness of about 1.8 to 2 mm and contains the following composition by weight: collagen 70.3%, plasticizer (typically glycerol or glycerine) 16.9%, water 9%, other 3.8%. Such a material is available from Norwood Medical Products Division of Norwood Industries, Inc., Malverne, Pa.

When gelatin or other water soluble forms of collagen are utilized, certain advantages are provided in that the material will readily polymerize at body temperatures to form a stable subcutaneous gel. In addition, when implanted into the body as filler material in the weld joint, the polymerized material will become rapidly populated by host fibroblasts. Thus, the material becomes vascularized and can remain histologically, stable for up to 18 months. One problem with gelatin material per se, however, is that it is highly soluble in blood such that the flow of blood across the material will cause it to dissolve. Thus, gelatin or other soluble collagen material when used alone as laser weld filler should be limited to areas where direct contact with blood is avoided or minimized.

It is more advantageous to use mixtures of the various types of collagen to obtain the most desirable features of each grade. For example, a 50/50 mixture of Semed F and Semed S allows the joint to obtain the higher tensile strength values of the F grade while retaining the superior flow properties of the S grade. Proportions ranging from 3:1 to 1:3 also form useful mixtures. In addition, the gelatin material described above can be used in combination with the Semed F to achieve similar results.

In addition, low melting polymers or polymeric materials such as copolymers of polyhydroxy buteric acid and valeric acid are useful in certain applications. Plasticizers such as polysaccharides may be included to further lower the melting point of these copolymers to below 200° F. These polymers may also be mixed with the collagen or gelatin to increase the strength of the final weld joint. The melting

TABLE I

| TYPE | WAVELENGTH ($\mu$) | F | ENERGY RANGE/PHOTONS | PENETRATION | COMMENTS |
|---|---|---|---|---|---|
| CO2 | 10.6 | $2.8 \times 10^{13}$ | $3.7 \times 10^{19}$ | microns | low penetration |
| Helium-Neon | .634 | | almost nil | nil | target laser |
| Neodymium - Multiple Harmonics | | | | | |
| Yag | 1.06 | $2.8 \times 10^{14}$ | $5.3 \times 10^{18}$ | high | yttrium-aluminum garnet |
| | 0.532 | $5.6 \times 10^{14}$ | $2.7 \times 10^{18}$ | Welds tissue at low energy | Increasing penetration increasing |
| | 0.353 | $8.4 \times 10^{14}$ | $1.8 \times 10^{18}$ | | |
| | 0.266 | $1.1 \times 10^{15}$ | $1.3 \times 10^{18}$ | | |
| Argon | 4.8 | $1.1 \times 10^{14}$ | $3.8 \times 10^{19}$ | 2–400$\mu$ | water absorption |
| | 5.12 | | | | |
| Excimer (Excitable dimer) | | | | | |
| Xe CL | .308 | $9.7 \times 10^{14}$ | $1.6 \times 10^{18}$ | <20$\mu$ | very short |
| Xe F | .351 | $8.6 \times 10^{14}$ | $1.8 \times 10^{16}$ | gasifies | operational |
| Kr F | .248 | $1.3 \times 10^{15}$ | $1.3 \times 10^{18}$ | calcified | distance |
| Ar F | .193 | $1.6 \times 10^{15}$ | $9.7 \times 10^{17}$ | plaques | increases safety |

TABLE II

Proposed Laser-Fiberoptic Systems

| Laser | Wavelength NM | Pulse Duration | Principal Fiber | Plaque Ablation | | Operating Range |
|---|---|---|---|---|---|---|
| | | | | Efficiency | Calcified | |
| Excimer | 248 | | | H | Y | ? |
| | 308 | 2–200 nsec | Silica | H | Y | L |
| | 351 | | | M–H | Y(?) | L |
| Argon | 488, 512 | 40 msec-CW | Silica | L–M | N | M–H |

TABLE II-continued

Proposed Laser-Fiberoptic Systems

| Laser | Wavelength NM | Pulse Duration | Principal Fiber | Plaque Ablation Efficiency | Plaque Ablation Calcified | Operating Range |
|---|---|---|---|---|---|---|
| Dye Laser | 450–800 | 1–2 μsec | Silica | M | ? | M |
| Nd:YAG | 1,064 | $10^{-9}$–$10^{-12}$ sec | None | H | N(?) | O |
|  |  | CW | Silica | L | N | M–H |
| Ha:YLF | 2,060 | 100 μsec | Silica | M | ? | M–H(?) |
| Er:YAG | 2,940 | 100 μsec | $ZnF_4$ | H | Y | H |
| $CO_2$ | 10,600 | 1 μsec | Halide (?) | H | Y(?) | ? |
|  |  | 10 msec | Halide | M–H | N | L |
|  |  | CW | Halide | L | N | L |

H, indicates high; Y, yes; L, low; M, medium; CW, continuous wave; N, no; Nd, Neodymium; Ha, Hafnium, Er, Erbium.
1, indicates extensive thermal damage; 2, strong water absorption; 3, possible mutagenicity; 4, nonthermal active mechanisms; 5, developmental fibers.

temperature of these polymers should be below about 212° F. and on the same order as the melting temperature of the collagen (i.e., between about 100°–200° F.).

A wide variety of energy sources may be used to provide the desired energy for effecting the weld repair. Typical laser devices are listed in Tables I and II. Low wattage laser energy devices, such as those utilizing argon or $CO_2$, would be the most useful for such welding because of their lower energy output. Higher energy output devices, such as electrostatic and RF frequency coagulators (available from Everest, ValleyLab, or Medtronics) using bipolar tips can also be used to denature or melt the collagen filler materials. Since these devices have greater power input, they can burn the collagen to a greater extent than the argon or $CO_2$ lasers. One skilled in the art, however, is able to control and successfully utilize these higher power devices in accordance with the teachings of the present invention.

An argon beam coagulator, such as those made by Beacon Laboratories or Birtcher, are also suitable since they provide an easily controllable flame or heat source which can be utilized to melt the filler material and surrounding tissue to form the weld joint.

Figure 1:
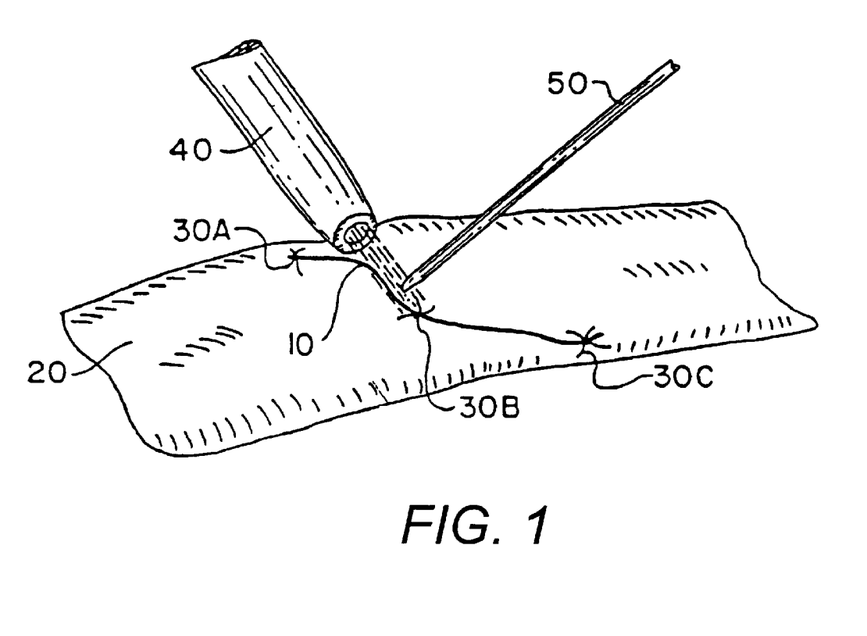
FIG. 1 is a perspective view of the use of a collagen welding rod for closing an incision in a blood vessel with the use of a laser or bipolar RF electrode.
Figure 2:
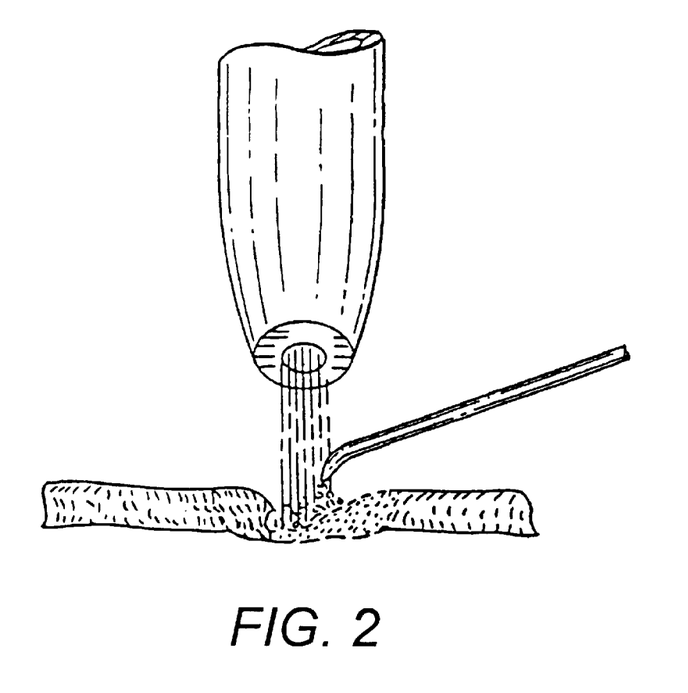
FIG. 2 is a detail of the denatured or melted collagen material in the weld joint of FIG. 1.

The protocol for the process is further appreciated by reference to FIG. 1. An incision 10 in a blood vessel 20 is closed by first applying three approximating sutures 30a, 30b and 30 followed by heating the tissue on either side of the incision with the laser 40. Filler material (e.g., collagen) is applied to the incision by placing the tip of welding rod 50 into the laser beam near the heated portion of the incision. The filler material 50 is literally melted (i.e., denatured) to provide additional collagen which flows onto or over the incision, mixes with the melted or denatured tissue, and thereafter cools and fuses to the underlying tissue substrate. FIG. 2 shows a detail of the joint as it is being made by this procedure.

As noted above, the use of such additional collagen material allows the tensile strength of the joint to be significantly increased over weld joints which do not include additional collagen filler material. This difference in tensile strength is due to the fact that the collagen filler material provides an additional collagen molecular substrate specifically in the area to be joined. The present technique therefore is analogous to the tungsten inert gas ("TIG") welding of metals such as steel or aluminum. In the TIG process, additional filler metal is almost always used on thin sections. Since the biological tissue to be joined is often relatively thin, similar improvements are obtained when using a filler material than by attempting to make the joint without such filter material.

It has been found that a $CO_2$ or argon laser with a half to one watt power is eminently suitable for making this type of joint. As noted above electrostatic generators can also be used. In addition, an argon beam electrocoagulator operated at 15–50 volts and 5–20 watts can also be used to denature and melt the collagen welding rod materials and surrounding tissue.

In an attempt to maintain the temperature of the tissue joint at a relatively low value, saline can be used. This is accomplished by dipping the collagen welding rod into saline prior to placing the saline dipped collagen welding rod adjacent to joint area or by dripping saline into the weld. In actual testing, saline cooling makes a different of approximately 23° C. in the joint area (e.g., about 47° C. compared to about 70° C. without saline cooling).

The present invention resolves many of the problems of the prior art. When welding biological tissues, it is difficult to achieve uniformly good results. This problem is due in part to the inability of the surgeon to uniformly melt the biological tissue on each side of the joint to obtain a satisfactory weld. With the use of collagen welding rod as proposed by the present invention, additional collagen material is supplied to the joint from the rod to compensate for any overmelting of tissue on either side of the joint. This also provides an abundance of additional material to seal voids or other defects caused by overheating of tissue. Thus, the reproducibility of the procedure and the attainment of uniform weld joints are significantly improved by the present invention.

All different types of biological tissue may be treated according to the present procedures. For example, all types of blood vessels, including veins, arteries, etc. in the vascular system can be connected or repaired, as can muscle, fascia, tendon, skin or even nerve material.

Figure 3:
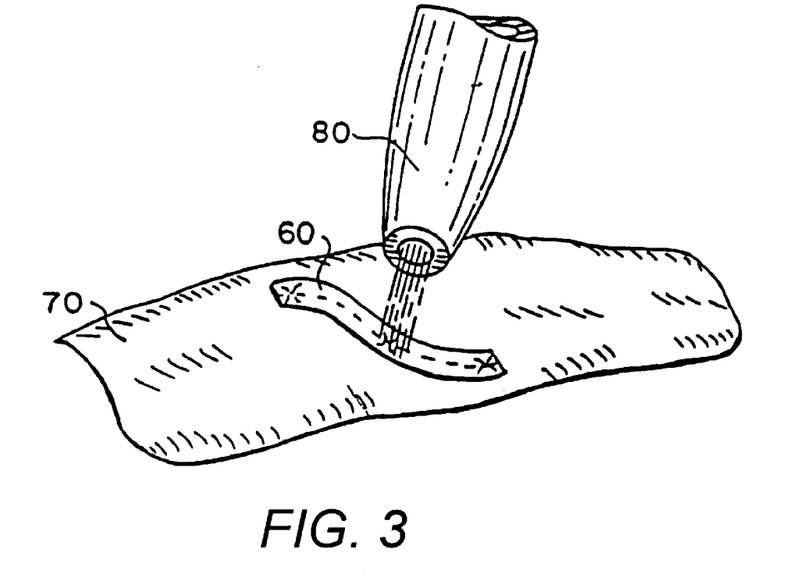
FIG. 3 is a perspective view of the use of a collagen strip in the laser joining of an incision.
Figure 4:
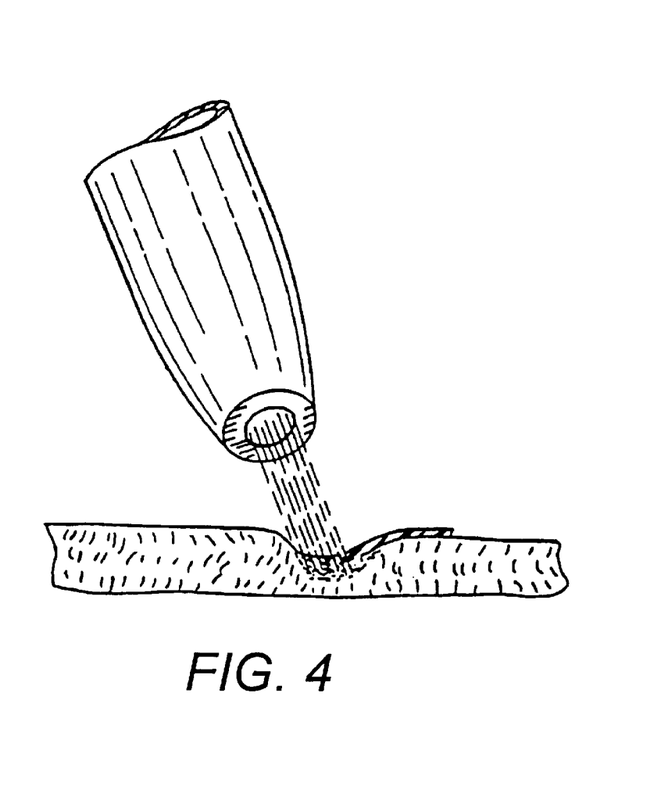
FIG. 4 is a detail of denatured or melted collagen material being applied upon a tissue defect or lesion.

Another procedure in accordance with the present invention is illustrated in FIG. 3. In that FIG., the incision is covered with a flat strip of collagen material 60 along its entire length. The adjacent blood vessel walls 70 on each side of the incision are overlapped by this strip 60 of collagen material. The laser 80 heats the strip of material and the adjacent blood vessel walls 70 to denature those materials into a mass which then solidifies to form the laser welded joint. Again, the use of the strip of collagen material 60 facilitates the welding operation and improves the resultant tensile strength of the weld joint. FIG. 4 shows a detail of the use of the strip material to fill a tissue defect or other lesion.

In an alternate embodiment of the invention, in order to insure that the placement of the welding rod remains in the appropriate position for allowing denatured collagen to flow into the joint area, it is possible to secure or attach the filler metal to the area to be joined. An easy way to accomplish this is to dip the filler material into fibrin glue prior to applying the filler material to the area to be welded. In addition to retaining the filler in the appropriate area desired, the fibrin glue or other biological tissue adhesive also appears to act as a flux which assists in directing the denatured or melted collagen material into the incision.

The welding procedure is made easier by utilizing an energy absorbing aid in conjunction with the filler material. These aids assist in the absorption of energy by the filler material so that the denaturing or melting process is more efficient, i.e., more of the energy is directly utilized to denature or melt the filler material rather than is scattered to other areas of the body near the tissue to be repaired.

Preferred energy absorbing aids include any of the numerous dyes, such as Vital Green or Basic Red. The color of the absorbing acid or dye should match the wavelength of the transmitted energy for optimum results. However, any substance, preferably which is in liquid form and which is capable of absorbing energy and transmitting the absorbed energy to the filler material, may be used. Often, the blood or hemoglobin of the patient may be used. Water or other physiologic solutions are also useful.

Advantageously, the energy absorbing aid is applied to the filler material to form a coating thereon. The filler material may simply be dipped into a reservoir of the energy absorbing aid. More complex arrangements, such as a spraying device or pump, can be used to apply the energy absorbing aid to the filler material, if desired.

In addition, the energy absorbing aid can be applied to the tissue to be repaired. This is easily accomplished, since the tissue is often cut and is bleeding to provide a suitable source of energy absorbing aid, i.e., blood. Also, the use of a dye is advantageous since it allows the joint to be easily viewed by the surgeon to determine exactly where the welding procedure must be conducted.

In yet another embodiment, the welding procedure can be performed endoscopically: i.e., access to the area desired to be repaired or reconstructed can be made through multiple naturally or surgically created apertures: one aperture is used for insertion of the laser, another for the insertion of the filler material, and a third for monitoring the procedure with an optical fiber connected to an eye-piece or a video camera while the procedure can be visually observed through the eyepiece or camera, the presentation of the procedure on a monitor is preferred because the incision can be viewed in an enlarged mode so that the surgeon can accurately determine the proper placement of the filler material and completion of the joint.

EXAMPLES

The following examples illustrate applications of the welding procedures of the present invention. A dog was anesthetized and its neck and groin area prepared for access. The carotid artery and jugular vein were exposed and clamped, and a one inch incision was made in each one. An argon laser operated at about one-half watt was used to reweld the clamped joints with one of Semed S, Semed F, and modified collagen material (i.e., gelatin) as described above. Sutures were included at each end of the incision to prevent propagation of the incision during welding.

The gelatin samples welded beautifully in that they readily melted, and simply and easily filled incision and rapidly formed a solid weld joint. However, upon exposure to blood, this material was solubilized by the blood which broke through the weld due to dissolution. The Semed F samples did not flow as readily into the joint, but once the joint was made, a very high tensile strength repair was obtained. The performance of the Semed S was intermediate between the modified polymer and Semed F both with respect to joint strength and fluidity. Mixtures of either Semed S or modified collagen (gelatin) with the Semed F material, in a 50/50 ratio provides the benefits of each material are achieved in a single filler rod material.

To aid in the absorption of energy by the filler material and the tissue to be repaired, Vital Green dye was applied to the tissue and filler material. The filler material was merely dipped into the dye. The dye coated filler and tissue greatly facilitated the welding operation as it was easier to apply the optical energy to the desired locations.

FIGS. 5–11 illustrate the usefulness of the welding procedures of the present invention by showing its effects on various welded tissue joints. These were generated by operating on dogs to incise normal tissue, followed by welding to repair the incision.

Figure 5:
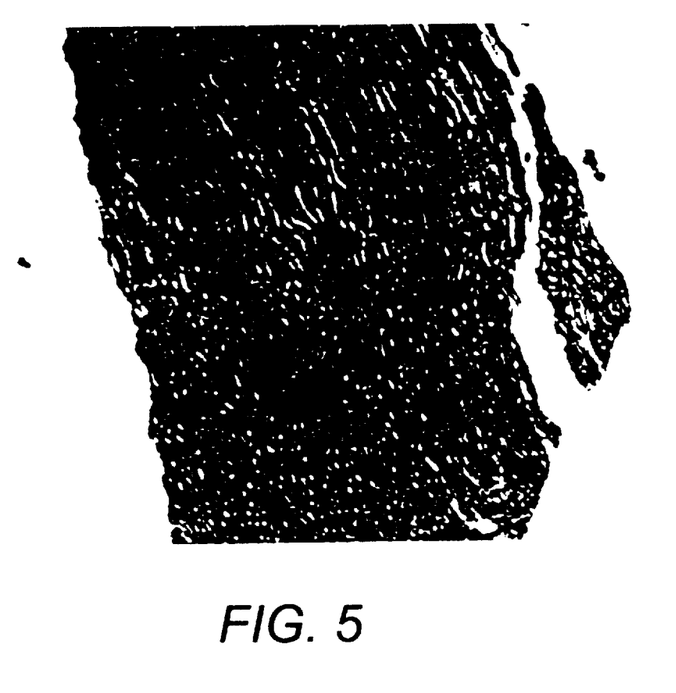
FIGS. 5–11 are photomicrographs which show the morphology of various welded tissue joints.

FIG. 5 shows the results of a dog aorta which was welded with the mixed collagen filler material two days after welding. The nuclei and cell structure of the aorta appear normal and no karyolysis is evident.

Figure 6:
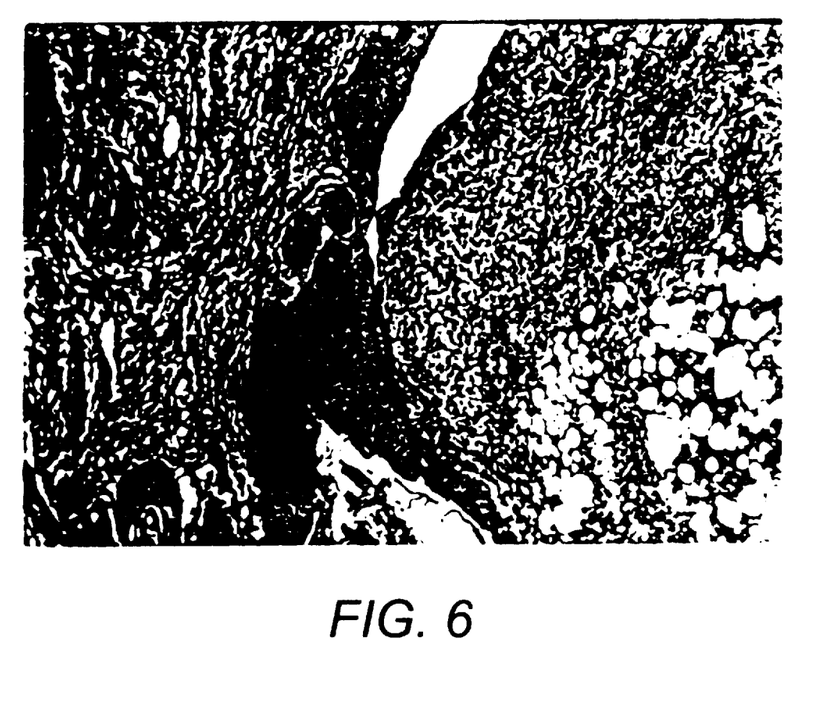

FIG. 6 shows this filler material and the welded vena cava adjacent the aorta of FIG. 5 two weeks after welding. The welded vena cava and collagen filler material are juxtaposed to form an intact weld joint across the incision. No evidence of thrombosis is seen at this joint or surrounding tissue.

Figure 7:
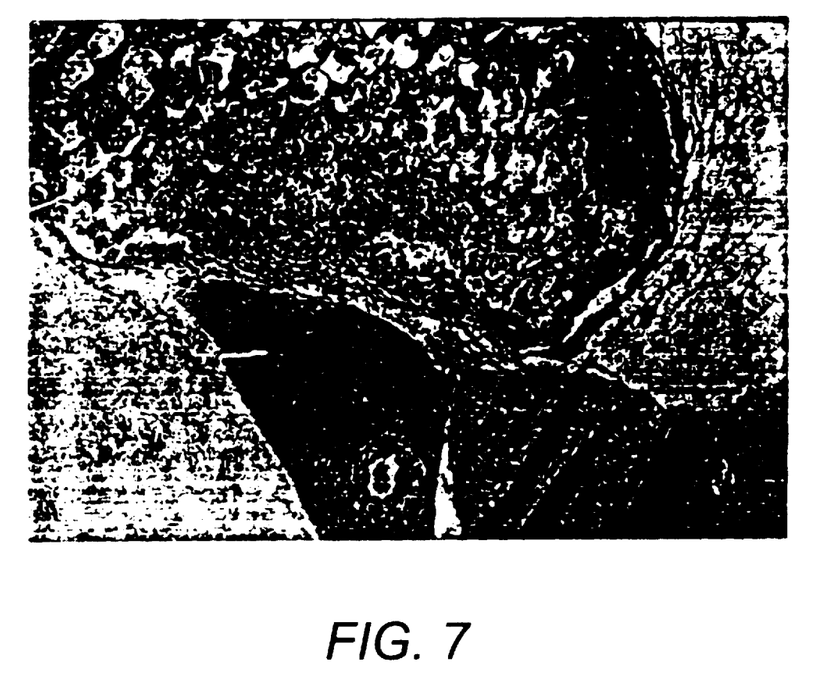
Figure 8:
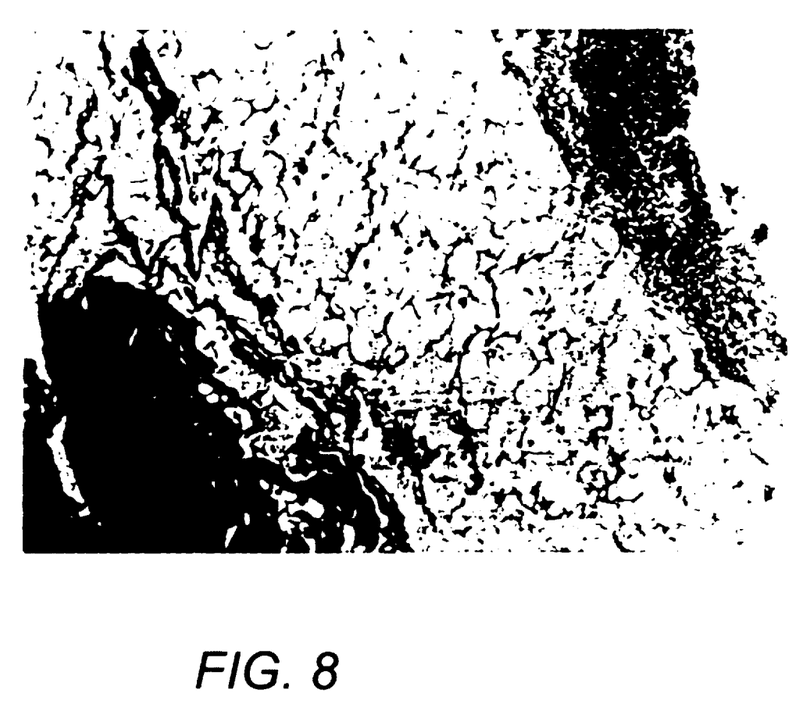

FIGS. 7 and 8 further illustrate the weld joint of FIG. 6. These FIGS. show the filler material bridging the incision. In FIG. 7, the collagen filler material appears as a large mass at the upper left hand corner of the photograph. The incision in the vena cava is just visible at the point where the material was transsected prior to placing in fixative. The fibrillar structure of the welding material is evident. In FIG. 8, a low concentration of welding material as a thin band bridges the incision which appears at the lower left corner of the photomicrograph. The incision is closed by this material, and the vena cava architecture is intact.

Figure 9:
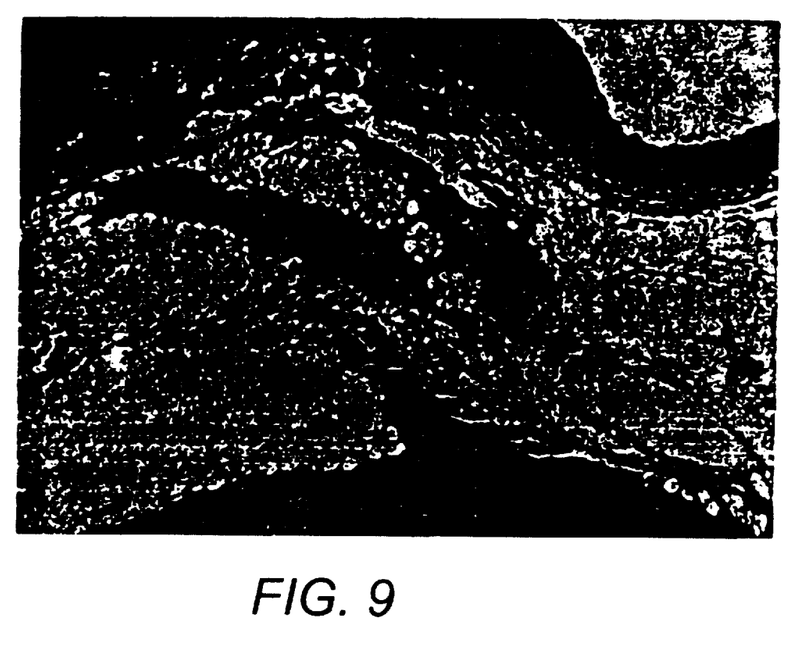

FIG. 9 illustrates welded skin tissue. The gelatin welding material bridges the incision but has relatively poor tensile strength when tested about ten minutes after making the weld joint. The weld joint was properly made and, as noted above, the strength of the welded joint can be improved by including collagen in the filler material.

Figure 10:
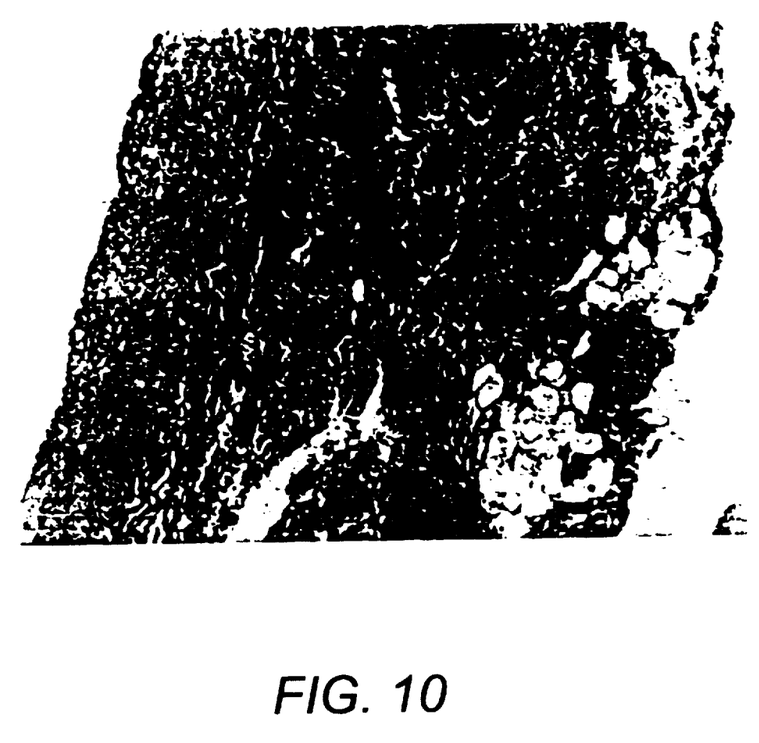

FIG. 10 illustrates a welded coating of gelatin material placed under the skin. The coating is able to hold the skin together for up to about ten minutes before losing strength due to saturation and dissolution in blood. Again, proper selection of a welding material which includes insoluble collagen will provide a higher strength coating.

Figure 11:
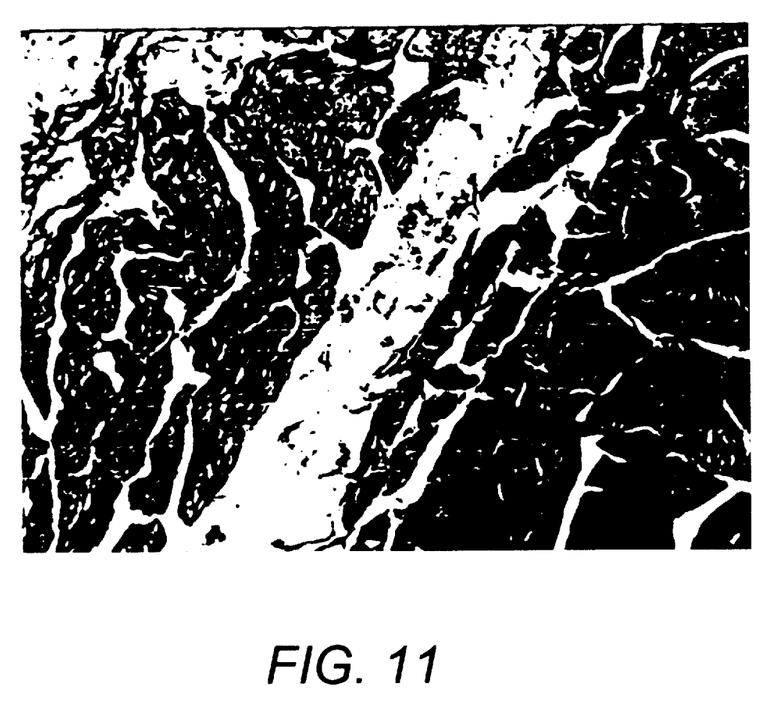

FIG. 11 illustrates the welding of muscle tissue with a mixed collagen filler material. The incision is clearly filled and joined by the welding material to produce a strong joint.

In the preceding FIGS., an Eximer $CO_2$ laser was utilized as the energy source, with basic red dye or blood used as the energy absorbing aid. No difference in performance was seen using either fluid.

A wide variety of devices can be used to place the welding material in the vicinity of the tissue to be repaired. For example, in addition to the above-described arrangements, a tube of collagen welding material can be placed concentrically around the laser. Thus, the surgeon can urge the tube forward toward the distal end of the laser, where it can be melted by the energy. The tube can be dyed with an energy absorbing aid to assist in the melting procedure. As the end of the tube melts, the surgeon can urge further material into the path of the laser beam. To retain the area to be repaired in the proper position, a pair of grasping forceps can also be used.

In addition, for the repair of a blood vessel, a catheter or stent which includes a tubular covering of filler material can be introduced into the vessel beneath the area to be repaired. Thereafter, the laser welding procedure is conducted on the outside of the vessel, to melt both the vessel and the collagen material which is immediately below. Again, if desired, the collagen material can be dyed to increase its absorption of energy and melting efficiency.

Both bi-polar and uni-polar RF electrodes were also utilized to denature or melt various samples of modified gelatin, Semed F and Semed S, both alone and in combination, into arteriotomies and venotomies. A vascular anastomosis was also crated using Semed F in accordance with the above-described welding technique. The weld joint was observed to be of high tensile strength. Also, attempts at approximating muscle, tendon and skin have been successfully completed.

It is believed that numerous variations and modifications may be devised by those skilled in the art to the specifically disclosed invention, and it is intended that the appended claims cover all such modifications and embodiments as would fall within the true spirit and scope of the present invention.

What is claimed is:

1. A method of joining or reconstructing biological tissue, said method comprising the following steps:

providing a solid filler material in the form of a preformed sheet, wherein the sheet comprises collagen, gelatin, or a mixture thereof;

placing the filler material over said biological tissue prior to applying energy, and applying radiofrequency or optical energy to the filler material in an amount sufficient to melt or denature the filler material while said filler material is over the said biological tissue.

2. A method as in claim 1, wherein the filler material is cut to a desired size prior to placing on the tissue.

3. A method as in claim 1, wherein the energy is radiofrequency energy applied from an inert gas beam coagulator.

4. A method as in claim 1, further comprising applying a tissue adhesive to the tissue prior to placing the filler material.

5. A method of joining or restructuring biological tissue, said method comprising the following steps:

providing a filler material in the form of a preformed sheet which fuses to said biological tissue upon the application of energy, wherein the filler material comprises collagen, gelatin, or a mixture thereof;

placing the filler material over said biological tissue to be joined or restructured prior to applying energy; and applying radiofrequency energy to the filler material in an amount sufficient to melt or denature the filler material and the said biological tissue after said filler material has been placed over the said biological tissue, wherein the radiofrequency energy is applied from an inert gas beam radiofrequency device.

6. A method as in claim 5, wherein the radiofrequency inert gas beam device is operated at between about 20 and 120 watts for about 1 to 60 seconds, so that about 20 to 1800 joules are delivered to the filler material and the biological tissue.

7. A method as in claim 6, wherein the radiofrequency inert gas beam device is operated at between about 35 and 80 watts for about 5 to 40 seconds, so that about 100 to 1200 joules are delivered to the filler material and the biological tissue.

8. An improved method for joining or reconstructing biological tissue wherein a collagen- or gelatin-containing material is placed over the tissue and energy is thereafter applied to fuse the material and tissue together, wherein the improvement comprises the step of applying radiofrequency energy to the material and said tissue under conditions which result in about 20 to 1800 joules of energy being delivered to the collagen or gelatin-containing material and the said tissue.

9. An improved method as in claim 8, wherein the collagen-containing material is in the form of a preformed a sheet.

10. An improved method as in claim 8, wherein the radiofrequency device is operated at between about 20 and 120 watts for about 1 to 60 seconds.

11. An improved method as in claim 8, wherein the radiofrequency device is operated at between about 35 and 80 watts for about 5 to 30 seconds, so that about 100 to 1200 joules are delivered to the collagen-containing material and the biological tissue.

12. An improved method as in claim 8, wherein the collagen-containing material is composed of a material selected from the group consisting of native collagen, collagen cast with a plasticizer, and gelatin.

* * * * *